United States Patent [19]

Pedersen

[11] Patent Number: 5,065,980
[45] Date of Patent: Nov. 19, 1991

[54] DIAPHRAGM VALVE

[76] Inventor: Borge C. Pedersen, Holstensvejen 26, 4534 Horve, Denmark

[21] Appl. No.: 539,659

[22] Filed: Jun. 18, 1990

[30] Foreign Application Priority Data

May 22, 1989 [DK] Denmark .............................. 2479/89

[51] Int. Cl.⁵ .............................................. F16K 7/16
[52] U.S. Cl. .................................... 251/144; 251/331; 137/241
[58] Field of Search .................. 251/144, 331; 137/241

[56] References Cited

U.S. PATENT DOCUMENTS

| 3,426,999 | 2/1969 | Toinet | 251/331 |
| 3,459,345 | 8/1969 | Chernak et al. | 251/331 X |
| 4,653,526 | 3/1987 | Hoiss | 251/331 X |
| 4,836,236 | 6/1989 | Ladisch | 251/144 X |

Primary Examiner—Arnold Rosenthal
Attorney, Agent, or Firm—Steve T. Zelson

[57] ABSTRACT

A diaphragm valve (2) comprising valve seats (11, 12) describing a sector of a sphere providing a complete closure of the inlet (13) and the outlet (14), when the diaphragm (16) assumes the shape of a spherical segment. The valve permits easy and complete cleaning and sterilization and is especially suited for sampling.

5 Claims, 4 Drawing Sheets

5,065,980

DIAPHRAGM VALVE

FIELD OF THE INVENTION

The present invention relates to the field of diaphragm valves, primarily to be fitted in a container wall, and comprising a valve casing with an inlet and an outlet channel and an interjacent diaphragm which can be pressed against and away from a valve seat for opening and shutting off the flow of a medium through the valve, and which valve is sterilizable by steam or other means.

The valve is suited for both vertical and horizontal mounting in said container wall for use both as a valve for taking samples and/or a drainage valve under conditions where strict hygiene and containment must be observed, such as in fermentation processes, biological experimentation and the like.

BACKGROUND OF THE INVENTION

Valves of this type are particularly used within the food, beverage, and medical industries where demands on hygiene are great. The presence of a diaphragm which separates the medium from the manoeuvring part of the valve makes this valve particularly suited for use in a sterile environment.

Also in recent years problems have arisen in connection with genetic engineering techniques, where authorities issue very strict rules about containment inside the fermentation tanks of genetically engineered microorganisms or cell lines for extended periods of time, such as 3 to 4 months for the fermentation of a cell line.

Hitherto known diaphragm valves have, however, turned out to give rise to problems, both in terms of failing sterile technical properties and in use in connection with sampling from the medium.

The diaphragm valve known from French patent No. 927,290 is an example of such a valve where the diaphragm rests on a valve seat being designed in a rib extending across the flow channel. This rib is provided with several pockets and corners in which the medium may be deposited so that the valve firstly is difficult to clean and sterilize, and secondly, will cause an uneven sampling, both since the uneven flow conditions cause an uneven mixing of the medium, and due to the risk of stagnant media. Also, the bad flow conditions cause a great loss of pressure.

French patent No. 1,200,849 (Nuyens) is another example of such a valve. However, the valve of that patent cannot be mounted so that the diaphragm in closed position forms a closure against the container wall and partly becomes an integral part thereof, but a stagnant container volume (dead volume or leg) will be formed in the valve inlet.

The valve cannot be used for sampling from suspended fluids, since the stagnant volume of fluid in the valve inlet will have a higher concentration of suspended material than in the container where the suspension is kept in mixture by stirring means.

Another example of a diaphragm valve of a related type is disclosed in U.S. Pat. No. 4,653,526 (Hoiss) relating to a diaphragm valve for removing samples from a pipeline. In connection with that patent corresponding problems relating to dead volumes in the valve inlet arise.

An example of a type of valve used as a sterilizable drain valve can be seen in U.S. Pat. No. 4,836,236 (Ladisch). The valve according to that patent also exhibits a valve chamber giving problems in connection with sterilisation and complete drainage of said chamber. Also, that type of valve is in no way suitable for vertical mounting for taking samples from the content of a tank.

A further disadvantage with many of the prior art diaphragm valves is that the diaphragm material during operation must be deformed considerably increasing the risk of cracks in or bursting of the diaphragm.

The reality of this problem is seen in that the valve in U.S. Pat. No. 4,836,236 is provided with special sealing means which safeguard against leakage by diaphragm rupture.

SUMMARY OF THE INVENTION

It is the object of the invention to overcome these shortcomings and disadvantages by providing a flush-mounting flush-sealing diaphragm valve for vertical or horizontal mounting for taking samples from or draining of a container, which valve further has the capability of complete steam sterilization in situ, and substantially without any sedimentation due to the presence of the valve.

The substantially flush-sealing diaphragm valves of the invention are especially directed at use in fermentation tanks and the like where genetically engineered microorganisms or mammalian cells are cultivated and where full containment is demanded with a view to protection of the external environment.

It is also important that the valve housing inlet and outlet and the diaphragm, which come into contact with the fluid, form a fluid-contacted volume being constructed by means of simple geometric forms ensuring optimal "sanitary standard" in an uncomplicated cleaning process. Remaining material, if any, which cannot be washed out of the valve forms a contamination risk even if the valve is sterilized with superheated steam before the fermentation cycle is initiated.

With a view to sampling during fermentation it is very important that a minor sample is absolutely representative of the container volume as analyses of the sample are used to control the fermentation process in the container.

It must be possible to sterilize the valve with steam in the valve outlet during the fermentation without damaging the culture in the tank during the sterilization so that sampling can be performed in a recently sterilized part of the discharge tube.

This is obtained by a diaphragm valve, wherein the valve housing forms an integral part of the container or tank (e.g. by being welded into the wall of the tank), the surface of the diaphragm in closed state is geometrically close to the inner outline of the container, the diaphragm closes and abuts directly against valve seats in both the tank outlet (valve inlet) and discharge tube (valve outlet) simultaneously, and wherein no permanent valve chamber is provided.

In a preferred embodiment means are provided for supplying steam or other sterilizing fluids to the valve outlet.

BRIEF DESCRIPTION OF THE DRAWING

In the following the invention will be described in further detail with reference to the drawing, in which.

DETAILED DESCRIPTION OF THE INVENTION

As indicated above it is the object of the present invention to provide an improved flush-mounting flush-sealing diaphragm valve for vertical or horizontal mounting for taking samples from or draining of a container, which valve further has the capability of complete steam sterilization in situ, and substantially without any sedimentation due to the presence of the valve.

The valve of the invention is shown in FIGS. 1 to 4 in embodiments which will be discussed in detail below.

The valve of the invention is a diaphragm valve especially suited for welding into a the side or bottom of a container depending on its mode of use.

The valve of the invention comprises:
a) a valve housing having a valve inlet port or opening communicating with the fluid inside the container, and an outlet port or opening for extracting fluid from the inside of the container,
b) a flexible diaphragm mounted movable for shifting between an open and a closed position, and
c) actuator means for shifting the diaphragm between the open and a closed position.

The valve of the invention is characteristic in that the valve housing forms an integral part of the container, whereby the valve inlet port also functions as a container outlet port or opening, and the surface of the diaphragm facing the inside of the container in the closed position is geometrically close to the inner outline of the container.

The valve is further characteristic in that the diaphragm closes and abuts directly against valve seats surrounding the valve inlet port (container outlet) and valve outlet port simultaneously so that the deformation of the diaphragm is uniform. The diaphragm further works in such a way that it seals the valve without the need for special sealing means in connection with the mechanism provided for moving the diaphragm between open and closed positions.

The valve housing is designed so that it when being mounted horizontally can discharge the contents of the container completely and also empty the valve housing completely when the valve is closed again.

Mounted vertically the valve housing can be drained completely in the valve inlet as well as in the valve outlet, this allows sampling of fluid that is 100% representative of the contents of the container.

The valve housing and position of diaphragm according to the invention as described further below give considerable sterilization safety upon use of superheated steam or of liquid under pressure in the container as stagnant medium in a dead volume at any position in the valve housing is effectively avoided.

Open sterilization is also optimal both to the valve inlet and the valve outlet, as well as to the inner surfaces due to the simple geometry.

Figure 4:
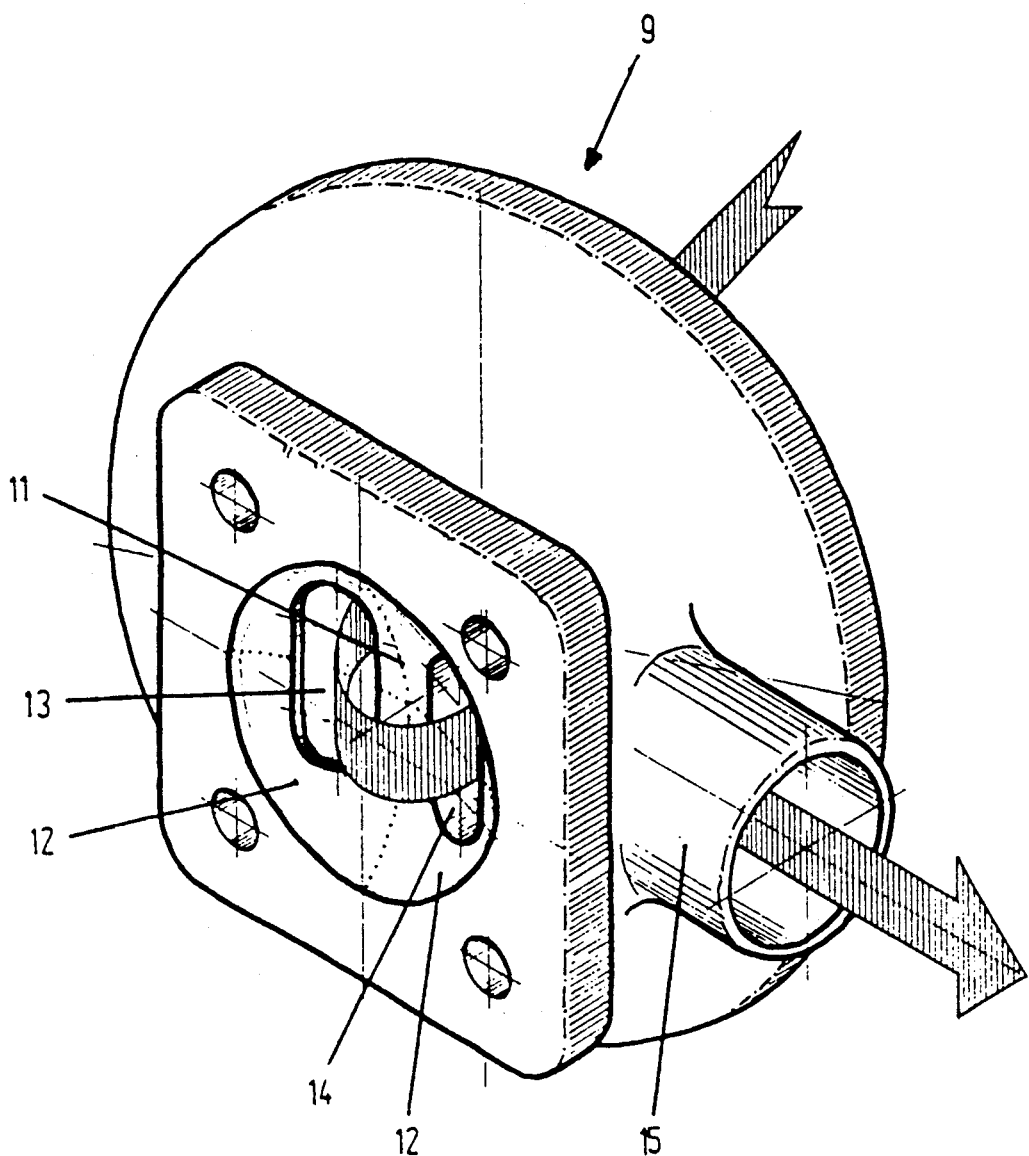
FIG. 4 is a perspective view of a diaphragm valve of the invention with the diaphragm removed and the flow indicated.

In principle the geometry of the valve housing preferably is so that the seats for the diaphragm, seen together as a whole as in FIG. 4, forms the contour of a section of the surface of a sphere having its centre outside the container. Hereby the diaphragm in the closed position takes form as a sector of a corresponding spherical surface sealing against the seats. By this an even and minimal deformation of the diaphragm is obtained, minimizing wear from deformation of the diaphragm.

By this configuration is first and foremost achieved the best possible closure of the inlet and the outlet in that once the diaphragm is pressed in, it will abut tightly on the valve seat under the formation of a spherical segment. The channels are hereby completely closed at the valve seats, and no cavity can occur between the diaphragm and the seats. The medium will thus be limited by the diaphragm, and a complete emptying of the channels can be ensured, which in turn ensures that for instance a sampling is representative of the medium.

Moreover, the diaphragm will shut off the inlet and outlet uniformly when the diaphragm is moved towards the seat which produces an advantageous flow characteristic and a uniform deformation of the diaphragm minimizing wear on both the valve housing and diaphragm.

If the inlet channel is narrowing toward the valve seat, as seen from the inside of the container to form a funnel-shaped channel, the best possible flow conditions are obtained for the inflow as well as for the outflow with practically no risk of stagnant media.

Finally, it is expedient to provide for channels in the outlet port for supplying disinfectant fluids to be able to sterilize the valve and outlet channel by adding steam or the like, or by adding a liquid, when the valve is closed.

The diaphragm sealing concentrates the heating effect to the valve housing and container as the diaphragm thermally insulates the remaining parts of the valve therefrom.

The valve housing can be made by material of uniform dimensions ensuring an even heating (and thereby expansion) when sterilization is performed.

The drawing shows an example of a preferred embodiment of a valve 2 being provided with an upper part for manual operation of the diaphragm. In the drawing a manual spindle mechanism is indicated, but it is of course within the scope of the invention to replace this upper part by another type of actuator such as a lever. The mechanism may of course also be remotely controlled by electrical or pneumatic means through, or through a motor drive or the like.

In the shown example the upper part comprises a flange 18 which is open at the centre for a spindle (not shown) which interlocks with an attachment piece 17 on the back of a diaphragm 16. A spindle casing 20 is secured to the flange 18, and an opening indicator 21 is secured at one end of the spindle casing 20. Finally, a handwheel 22 is attached which by turning moves the spindle and thus the diaphragm 16, 17.

The valve 2 comprises a valve casing 9 which is for instance made of stainless steel and provided with a base which, in the shown example, is designed so that the valve casing can be attached to a cut-out in a container wall 1 by means of a welded seam 6.

The inlet channel 13 is defined partly by an outwards slanting outer part of a flange 8 of the valve casing 9 and partly by a bottom wall 10 of the valve casing 9 slanting outwards from the opposite side.

An outlet channel 15 is defined partly by the opposite side of the bottom wall 10 and partly by an outer part 15 of the flange which defines the valve casing at the top.

In the shown example the outlet channel 15 is connected to a pipe 5 by a welding 7. Moreover, a pipe 4 opens into an opening 3 in the outlet channel 15 through which opening steam or the like for sterilization of this part of the system can be added. If there is no steam outlet through the outlet pipe 5, and outlet opening (not shown) can be arranged for the steam. These openings 3 can be provided with barriers (not shown) for the formation of a closed pipe system.

The diaphragm 16, 17 can be made of any suitable resilient material such as reinforced rubber, plastics, metal or the like, depending on the type of medium.

The diaphragm 16, 17 is placed on the outside of the flange 8 of the valve casing 9 and is secured by means of bolts 19 extending through the flange 18 of the upper part through the diaphragm 16 into thread holes in the casing 9. This facilitates an easy disassembly of the parts for purposes of inspection and replacement of the diaphragm, if so required.

The valve seats are designed partly as a circular seat 12 extending around inlet 13 as well as outlet 14, and partly as a seat 11 arranged in the bottom 10 separating the inlet 13 from the outlet 14.

Figure 1:
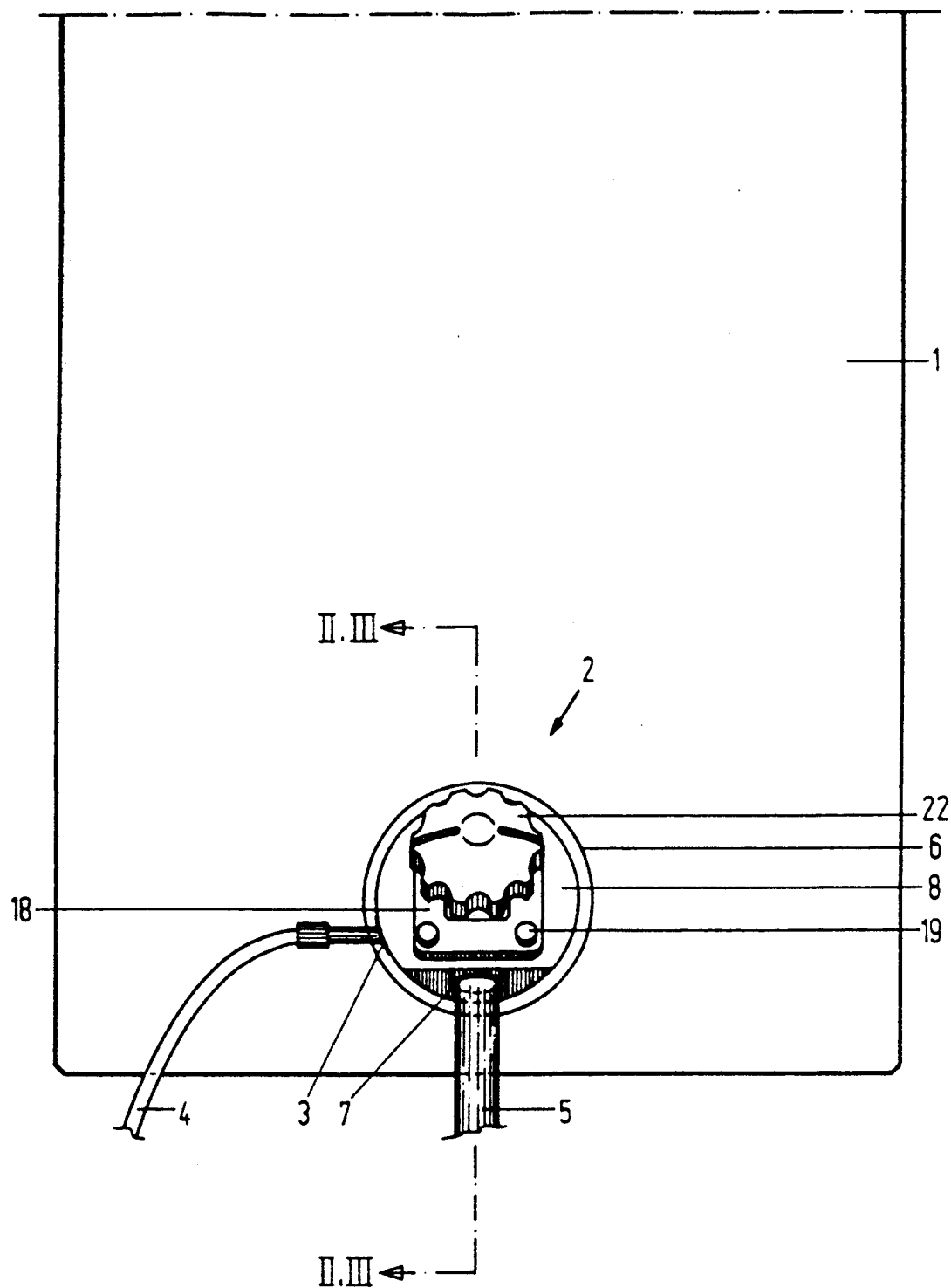
FIG. 1 shows a diaphragm valve according to the invention built into a container wall seen from the outside.
Figure 2:
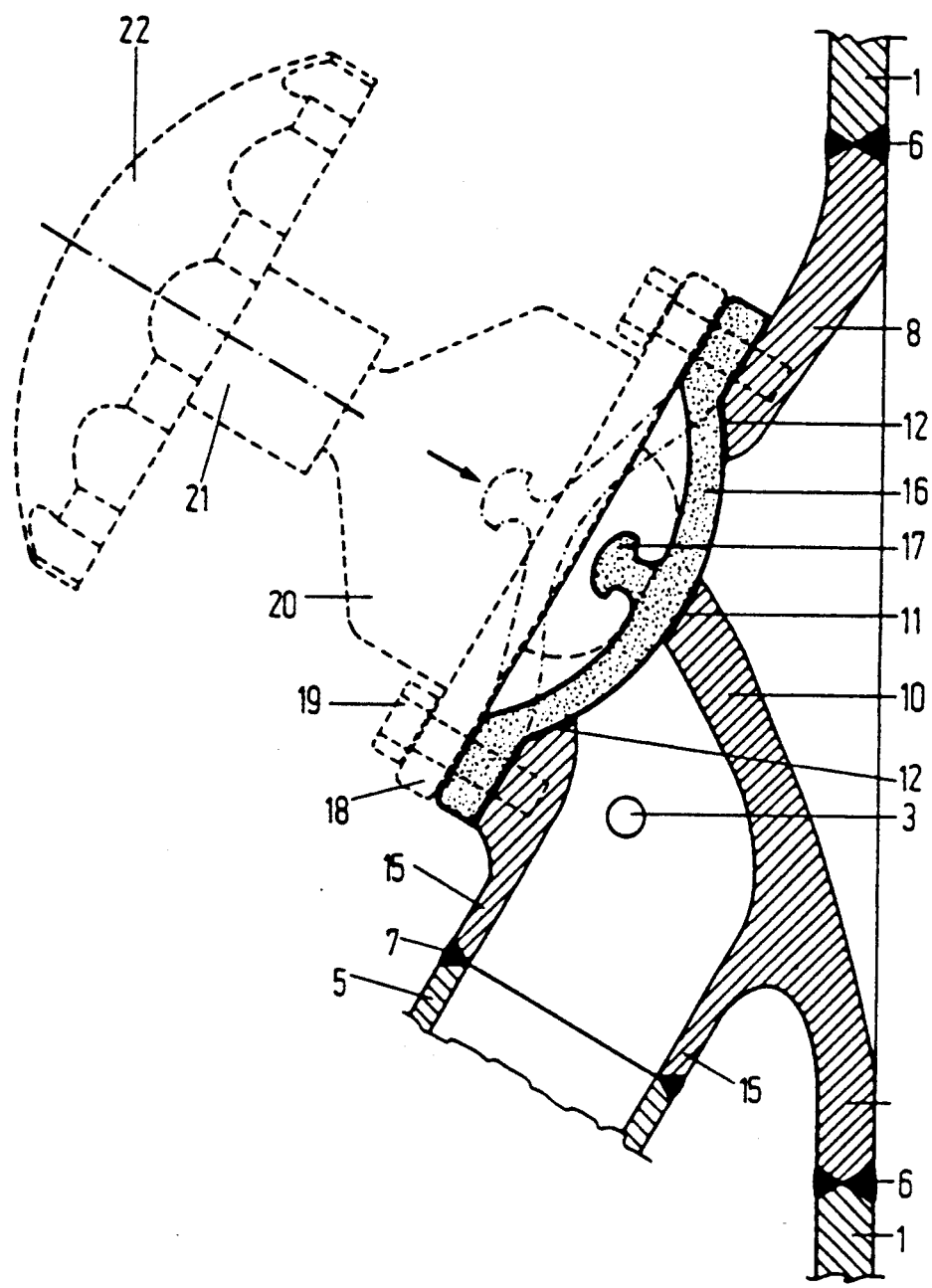
FIG. 2 is a sectional view of the closed valve, seen along II—II in FIG. 1.
Figure 3:
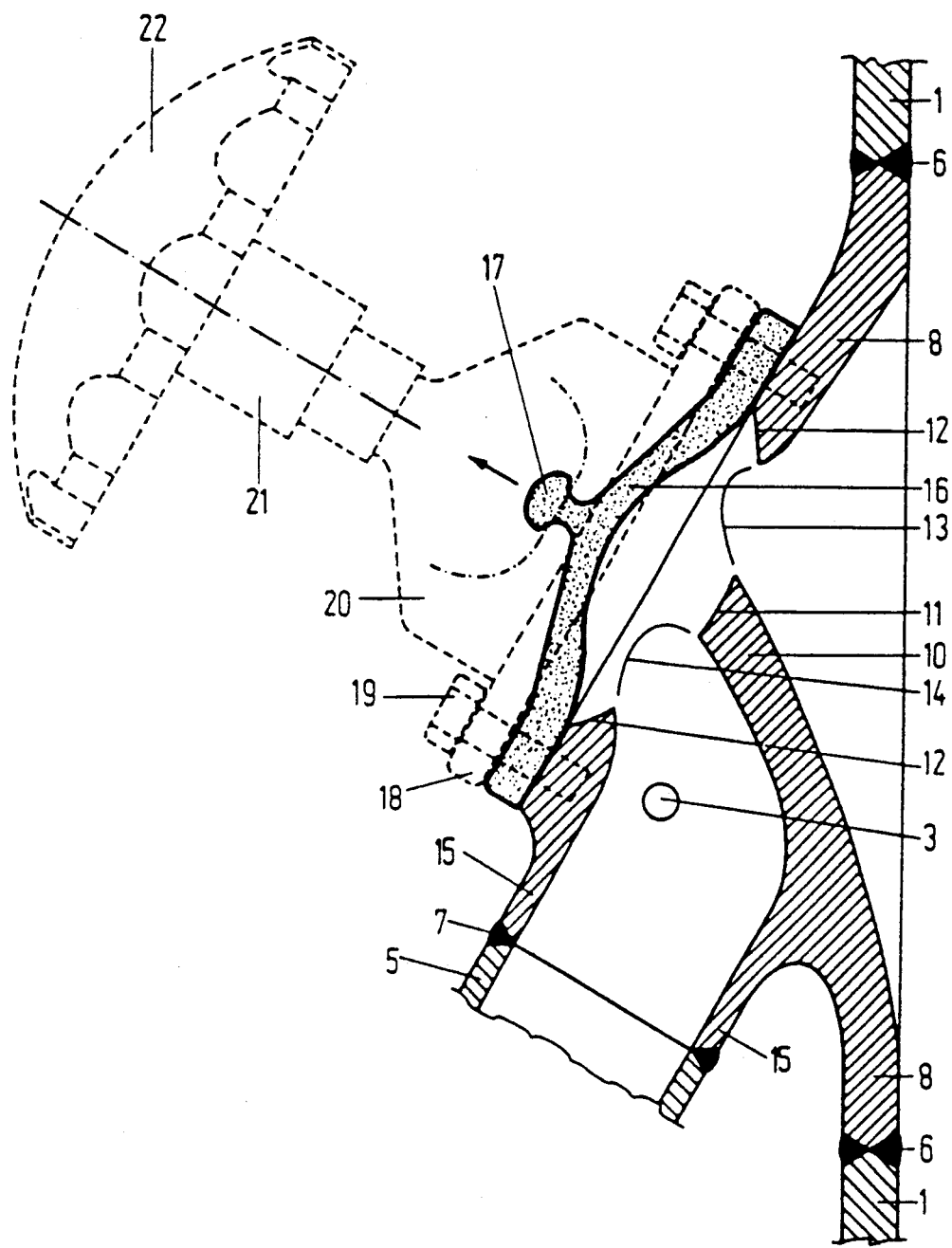
FIG. 3 is a sectional view of the open valve, seen along III—III in FIG. 1.

These valve seats 11, 12 have such a geometrical shape that they substantially define a sector of a sphere. Hereby optimum contact is obtained to the moving part of the diaphragm 16 from its outer to its inner rim in that the diaphragm will assume a shape corresponding to a spherical segment once it is pressed in for abutment on the valve seats for closure of the valve, as shown in FIG. 2.

This provides optimum sealing while at the same time the diaphragm separates the inlet 13 as well as the outlet 14 entirely from the inner rim of the valve seats 11, 12. Consequently, no pockets or corners can occur in which the medium may deposit, and the valve can therefore be emptied completely.

This provides the required guarantee that for instance a sampling will always be representative of the medium, and the construction facilitates a thorough sterilization, because the inner surfaces are freely accessible.

Finally, the valve has optimal flow conditions, and the loss of pressure through the valve will be held at a minimum.

I claim:

1. A diaphragm valve primarily to be fitted in a container wall, comprising:
   a) a valve housing (9) having a valve inlet port or opening (13) communicating with the fluid inside the container, a valve outlet port or opening (14, 15) for extracting fluid from the inside of the container, and valve seats (11, 12) surrounding the valve inlet port (13)
   b) a flexible diaphragm (16, 17) mounted movable for shifting between an open and a closed position, and
   c) actuator means (22) for shifting the diaphragm between the open and a closed position, wherein the valve housing (9) forms an integral part of the container, whereby the valve inlet port (13) also functions as a container outlet port or opening; the surface of the diaphragm (16) facing the inside of the container in the closed position is geometrically close to the inner outline of the container, and abuts directly against the valve seats (11, 12) surrounding the valve inlet port (13) and valve outlet port (14) simultaneously closing both the valve inlet and outlet ports (13, 14) with uniform deformation of the diaphragm.

2. The diaphragm valve according to claim 1, wherein the valve seats (11, 12), seen together as a whole, forms the contour of a section of the surface of a sphere having its centre outside the container, whereby the diaphragm (16) in the closed position takes form as a sector of a corresponding spherical surface sealing against the seats (11, 12).

3. The diaphragm valve according to any one of claims 1 or 2, wherein the inlet channel of the valve casing (9) forms a funnel-shaped channel opening on to the inlet (13) of the valve seat (11, 12).

4. The diaphragm valve of claim 1 or 2, wherein an opening (3) and an optional outlet for steam or a similar disinfectant open on the outlet channel (15) of the valve casing (9).

5. The diaphragm valve of claim 3, wherein an opening (3) and an optional outlet for steam or a similar disinfectant open on the outlet channel (15) of the valve casing (9).

* * * * *